United States Patent [19]

Collins et al.

[11] 3,941,606
[45] Mar. 2, 1976

[54] METAL CARBOXYLATE-ALKOXY ALCOHOLATE COMPOSITION AND PROCESS

[75] Inventors: Albert V. Collins, Fairview Park; Richard E. Pearl, Cleveland, both of Ohio

[73] Assignee: Mooney Chemicals, Inc., Cleveland, Ohio

[22] Filed: Nov. 12, 1973

[21] Appl. No.: 414,654

Related U.S. Application Data

[63] Continuation of Ser. No. 164,426, July 20, 1971, abandoned.

[52] U.S. Cl. .............................. 106/243; 106/310
[51] Int. Cl.² ............................................ C09F 9/00
[58] Field of Search .......................... 106/310, 243

[56] References Cited
UNITED STATES PATENTS

| | | | |
|---|---|---|---|
| 2,251,798 | 8/1941 | Meidert | 106/310 |
| 2,807,553 | 9/1957 | Fisher | 106/243 |
| 2,955,949 | 10/1960 | Kirshenbaum | 106/310 |
| 3,124,475 | 3/1964 | Fisher et al. | 260/414 |
| 3,499,742 | 3/1970 | Kivelevich | 44/76 |
| 3,686,012 | 8/1972 | Fisher | 106/310 |
| 3,702,822 | 11/1972 | Hansen | 252/37 |
| 3,723,152 | 3/1973 | Alkatis | 106/310 |

FOREIGN PATENTS OR APPLICATIONS

| | | |
|---|---|---|
| 1,148,998 | 4/1969 | United Kingdom |
| 1,528,804 | 5/1968 | France |

*Primary Examiner*—Theodore Morris
*Attorney, Agent, or Firm*—P. D. Golrick

[57] ABSTRACT

Metal carboxylate-glycol or carboxylate-glycol ether compositions, useful as siccatives in paint and like coating drier compositions, as internal combustion engine fuel—and other fuel—additives, and as stabilizers for polyvinyl chloride type plastics, and soluble in linseed oil and in aliphatic and aromatic hydrocarbon solvents, are prepared in liquid form by heating a mixture of (a) an appropriate metal powder or compound such as an oxide, hydroxide, acetate, or carbonate, (b) a branched chain aliphatic or a non-aromatic cyclic carboxylic acid, even an acid as low as a five carbon acid, or a mixture of such acids, and (c) a polyol or an alkoxy alkanol, e.g., a glycol or glycol ether; and, after filtration of the reaction mix, distilling off any volatile reaction by-product and also excess glycol or glycol ether. Higher than the usual equivalents of metal may be reacted for each equivalent of acid used. Certain of the products have remarkably low viscosity without special dilution. The products are believed to be metal carboxlate-glycolate, -ether glycolate-alcoholate complexes.

18 Claims, No Drawings

METAL CARBOXYLATE-ALKOXY ALCOHOLATE COMPOSITION AND PROCESS

This application is a continuation in part of co-pending application Ser. No. 164,426, filed July 20, 1971, now abandoned.

For incorporation of the many polyvalent metals known to be catalytically effective as driers in paint, varnish, ink and other coating compositions, or useful as fuel additives, for example, the history of the pertinent technology is replete with proposals of many metal compound types, ranging from the oxides and simple inorganic compounds, through organic compounds of various complexity. Particularly widely used have been the normal or basic salts or soaps with various natural though usually refined organic acids, notably natural straight and branched chain carboxylic acids and mixtures such as tall oil acids, cyclic carboxylic acids such as naphthenic acids, and as well various synthetic carboxylic acids. Cost reduction, uniformity of product especially through use of more uniform or standardized reactant starting materials, or provision of characteristics particularly desired either in the metal composition products themselves, or in their behavior in or the behavior of the compositions with which they are ultimately used have been goals sought, especially in the many drier compositions developed.

Thus a high drying efficiency, compatability with other constituents of a coating or other composition in which ultimately used, solubility in other constituents incorporated in such coating compositions, stability of the final composition including the continued effectiveness of the drier, the ultimate influence on the final coating or other ultimate product as used, have all been considerations in the pursuit of or choice of new compositions. By practical considerations in the manufacture and distribution of such compounds and as well in their ultimate use in larger compositions, ready solubility of especially metal salts or soaps in hydrocarbon solvents as carriers, low viscosity, and stability of the resulting solutions on storage and as well of the original metal compounds themselves, have been characteristics sought.

As technology developed for synthesizing heavier aliphatic carboxylic acids, or at least standardizable mixtures thereof, containing six or more carbons and having, as compared with natural acids or acids derived from natural products, the advantages of lower cost, greater reliability of supply, and uniformity of the synthetic starting acid materials, favored their use for preparation of normal or basic salts or soaps analogous to those of the prior art. Some idea of the scope of prior practice is given, by both the disclosures relating to their own inventions and by their discussion of certain art prior to them, in the U.S. Pat. Nos. 2,251,798 of Meidert el al., 2,955,949 of Kirchenbaum et al., and 3,124,475 of Fischer et al., the inventions of which were directed to preparing such compositions from synthetic carboxylic acids.

These patents represented variations on the common theme and teaching of the first named, Meidert et al., that the extensively branched saturated aliphatic carboxylic acids — with the numerous polyvalent metals therein stated to be known in the prior art as suitable drier metals — form/normal and basic salts or soaps marked especially (a) by good solubility, for example, in linseed oil and hydrocarbon solvents and by the considerably lower viscosity of such solutions, as compared with the corresponding salts of the saturated fatty acids having a normal unbranched carbon chain; and (b) in having favorable characteristics and behavior as to the storage and stability of the drier solutions as well as of the varnishes, lacquers or paints in which they are incorporated.

Whereas the normal or basic metal soaps of synthetic carboxylic acids, as proposed with advance of the acid Synthesis technology, have been compounds analogous to those previously derived from natural acids, or in using different synthetic carboxylic acids as they become available have presented compounds with a more or less homologous if not isomeric relation to each other, the present invention is a departure from prior art, marked by an essential difference in method of preparation and further in the composition structure and/or character and properties of the resultant drier product or metal soap.

By the prior art, the metals soaps are prepared generally by fusion or precipitation methods. A more common variation of fusion preparation comprises dissolving the reactant acid material in an appropriate inert solvent, usually a hydrocarbon solvent such as mineral spirits, to which then is added the desired metal component usually in the form of an appropriate oxide or simpler (usually inorganic) compound or salt; with heating at appropriate temperatures, to result in a hydrocarbon solution of the soap, perhaps after distilling off some of the excess solvent to produce a desired product concentration.

By the present invention an appropriate carboxylic acid or acid mixture, which may be natural in origin or derived from a natural product, such as aliphatic fatty acids, naphthenic acid, or tall oil acid or a synthetic acid such as alkoxy and phenoxy fatty acids, ether and thioether monocarboxylic acids, isopentanoic acid, 2-ethylhexoic acid, isooctanoic acid, isononanoic acid or a neo acid, e.g., neodecanoic acid (versatic acid), is dissolved in a simpler glycol, glycol ether or like polyl, with addition also of a reactant source of the desired metal, in the form of the metal powder, or of an appropriate oxide, hydroxide, or acetate or other simple salt, the resultant mixture being heated at a medium high temperature until the reactant metal source disappears or reaction is otherwise known to have been completed, and then, after filtering, distilling off substantially all water or other volatile products of reaction or present in the raw materials, and also excess glycol or glycol ether to an appropriate desired concentration or condition. A significant amount of the glycol or glycol ether must however be retained in the product.

Thus where three equivalents of litharge, one of isononanoic acid and two of ethyl Cellosolve (2-ethoxyethanol) as the glycol ether are heated in the range of 150° to 170°F., the litharge substantially completely reacts and disappears, and after filtering while yet hot and then vacuum distilling the reaction mix to remove water and excess Cellosolve until a lead concentration of 48% is reached, the product has a remarkably low room temperature viscosity, enabling ready use in paint formulations and the like without dilution; and has further complete linseed oil miscibility as well as complete mineral spirits solubility. However, in a process modification, a hydrocarbon solvent, e.g., mineral spirits, may be used in the reaction batch especially when the product is to be used in a solution of such solvent.

In similar fashion, per one acid equivalent, with various acids, and glycols or glycol ethers, three or more equivalents of litharge are completely convertable to a hydrocarbon-soluble and linseed oil-soluble form, as products having a negative acid number.

Equivalent ratios of metal/acid have been attained up to about 4/1.

Barium-, nickel, and manganese-containing compositions have similarly been prepared; and cobalt-containing compositions also, though by a method modification or variation.

It has been observed that where a glycol or other polyol is used in place of a glycol ether, product viscosities (though lower than for comparable prior art salts) are increased; and also that, where for example methyl Cellosolve (2-methoxyethanol) is used in place of ethoxyethanol lower viscosities result for a given metal content.

In the procedure, as hereinafter exemplified, it has been found possible to use, for example, the following alkoxy alkanols or polyols, in place of the Cellosolve (2-ethoxyethanol): methyl Cellosolve, Carbitol, i.e., diethylene glycol monoethyl ether or 2-(2-ethoxyethoxy) ethanol, butyl Cellosolve (2-butoxyethanol), diethylene glycol, triethylene glycol, dipropylene glycol, tripropylene glycol, polypropylene glycol, tetraethylene glycol, and also polyols, e.g., ethylene glycol and sorbitol. Mixtures of glycols and glycol ethers can be also used.

It also will be noted that the above named glycols or polyols and glycol ethers all fall within the following formula:

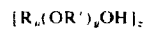

wherein
R is a hydrogen or an alkyl radical having from 1 to 10 carbon atoms;
$n$ is 0 or 1;
R' is an alkylene radical having 2, 3, or 4 carbon atoms which may be substituted with hydroxyl groups;
the value of $y$ is 0, 1, 2, 3, or 4; and
$z$ has a value of 2 when $n$ is zero, and a value of 1 when $n$ is 1 and R is hydrogen or alkyl.

In the method or preparation, where the alkoxy alkanol material to be reacted with the organic acid and metal is more volatile than any hydrocarbon permissibly to be used under any commercial process consideration, the alkoxy alkanol may be used in excess, by the excess to provide the reaction medium. Cellosolve (2-ethoxyethanol) was generally selected because of its favorable volatility and because of its efficacy in yielding products of lower viscosity.

The product and process thus are clearly distinct from proposals of prior art such as the use of varying amount of glycol or glycol ether, merely to reduce the viscosity of a basic lead carboxylate for various purposes, as in British Pat. No. 1,148,998; or to stabilize soap solutions as in Fischer U.S. Pat. No. 2,807,553. It is possible to prepare similar compositions in a mineral spirits medium, provided that an excess glycol, i.e., polyol, and/or glycol ether is used with all of the alkoxy alkanol material present from the start. It is preferred not thus to employ the hydrocarbon, especially with Cellosolve, because it is less volatile than Cellosolve, and there would be both glycol ether and mineral spirits by-product distillates to remove and purify for reuse; unless there is used a glycol ether less volatile than mineral spirits, but then product viscosity would be raised by the use of a higher boiling glycol ether.

In the presentation of various examples, hereinafter, Gardner values will be used for viscosity (at 25°C) and color; and for convenience and brevity, certain abbreviations are used as follows:

ABBREVIATIONS

| | |
|---|---|
| AN | Acid number (when negative, base number) |
| MS | Mineral spirits |
| IPA | Isopropyl Alcohol |
| C8 Acid | 2-ethylhexoic acid (AN 380) |
| C9 Acid | Isononanoic acid (AN 353) |
| C9-13 Acid | Mixture of 9 to 13 carbon neo acids (AN 360) |
| ND Acid | Neodecanoic acid (AN 320) |
| L-5 Acid | Tall oil fatty acid (AN 188) |
| M/A | Ratio of equivalents of metal (M) to equivalents of organic acid(s) (A) present in the final product |
| M/Alk | Ratio of equivalents of metal (M) to equivalents of polyol(s) and/or glycol ether(s), i.e., alkoxy alkanol(s) present in the final product |
| %G | Percent polyol and/or glycol ether by weight in the final product with respect to the organic acid present |
| LOM | Linseed oil miscibility |
| NVM | Non-volatile material |
| SR | "Solvent ratio", later defined |
| ( ) | Mole fraction of reactant (litharge; acid; glycol or glycol ether; etc.) |

In the tabular arrangement of the data used for several of the later examples, the left column presents all of the reactants, solvents, or other components put into the reaction batch; while the process conditions and product properties are in the right column.

EXAMPLE 1

A laboratory batch of the new type product containing 48% lead was made using
520 g litharge (PbO)
252 g C9 Acid
668 g Ethyl Cellosolve (2-ethoxyethanol),
as follows.

All of the isononanoic acid and 334 grams of the Cellosolve (herein "Cellosolve" without qualification signifies Ethyl Cellosolve) were charged into a reaction vessel and the batch heated to 150° F, i.e., about 65° C. The litharge was slurried with 267 grams of the Cellosolve, and gradually added to the reactor, while increasing the batch temperature to 170°F, all residual slurry being rinsed into the batch with 67 grams of Cellosolve. The batch was maintained for reaction at 170° F, i.e., about 77° C, until it developed a cream-colored, appearance and the litharge has substantially disappeared; the reaction time being about 3 ½ hours.

The crude product, containing approximately 40% lead, was filtered hot, and then vacuum distilled to remove water and excess Cellosolve, concentrating the product to 48% lead.

The batch would produce about 42 grams of by-product water to be stripped off at 200mm Hg, and form about 49 grams of discarded azeotrope. At higher pressures the azeotropes would be richer in Cellosolve, and a larger cut would have to be taken. The balance of the Cellosolve distillates would be relatively dry, and satisfactory for re-use in the manufacture of another batch.

Larger amounts of Cellosolve have also been used as a reaction medium, but there is no apparent advantage in such usage.

The liquid product has the characteristics and properties as set forth in the following Table I.

TABLE I

| Properties of Product of Example 1 | |
|---|---|
| %Pb | 48.1 |
| %NVM | 85.2 |
| Acid Number | −166 |
| Metal/Acid Ratio | 3.0 |
| Color | 5 |
| Viscosity | J |
| LOM | Complete |
| MS Solubility | Complete |
| Flash Point, °F (Min.) | 104°F |
| Specific Gravity 25/25°C | 1.780 |
| Weight Per Gallon, Lbs. | 14.83 |
| Net Weight, 55-Gallon, Lbs. | 800 |

This product is quite fluid at normal temperatures with surprisingly low viscosity in view of a lead content one-third greater than any similar liquid drier presently commercially available; though, of course, at low temperatures its viscosity increases without, however, freezing by virtue of the excess content of Cellosolve, represented by that 15% of the product which is expellable by further heating.

The product can be reduced with mineral spirits from 48% lead to other standard drier solution concentrations, such as 36%, 24%, and 16% lead, at which the viscosities are lower than for other lead driers now available at these concentrations. For drier use, one gallon of the 48% product will replace 3.1 gallons of 24% lead naphthenate, or 1.8 gallons of 36% lead trimethyl heptoate.

EXAMPLE 2

The procedure of Example 1 was carried out using

| | |
|---|---|
| 149 g | PbO |
| 121 g | naphthenic acid (AN 207) |
| 200 g | Cellosolve | so that again the equivalent ratio of the litharge to acid is 3/1 based upon apparent molecular weights and acid number. The litharge reacted substantially completely.

After vacuum distilling off excess Cellosolve until a 42% lead content was attained, the liquid product has the characteristics and properties as set forth in the following Table II.

TABLE II

| Properties of Product of Example 2 | |
|---|---|
| %Pb | 42.0 |
| % 2-ethoxyethanol | 20.7 |
| % combined naphthenic acid | 37.3 |
| %NVM | 90.8 |
| Metal/Acid Ratio | 3.0 |
| Viscosity | Z |
| LOM | Complete |
| MS Solubility | Complete |

Analysis showed the non-volatile content of the composition to be 90.8%; and since the composition contains 20.7% ethoxyethanol, with only 9.2% of the composition volatilizable, it is indicated that the other 11.5% ethoxyethanol has been converted to a non-volatile derivative.

EXAMPLE 3

A reaction mixture comprising

| | |
|---|---|
| 572 lbs. | PbO |
| 40 lbs. | neo-acid blend (AN 363) |
| 121 lbs. | isopentanoic acid |
| 868 lbs. | Cellosolve | prepared by slurrying the litharge in the Cellosolve, adding the acids (representing a metal-to-acid equivalent ratio of 3.50), was reacted by refluxing for 2 hours. The batch was cooled, clarified with diatomaceous earth and filtered; and by vacuum distillation the filtrate was concentrated to 49.3% lead.

The product liquid, after diluting to 48.1% lead with pure Cellosolve, had a density of 15.00 pounds per gallon, Gardner color of 4+ and viscosity of A-5; and is miscible in linseed oil, though having a water content of 0.46%.

Further to demonstrate the method of preparation of the new type of compositions with various acids and acid mixtures, glycols, other polyols and glycol ethers and mixtures thereof, the following further examples are given. In all these examples, (following the general procedures of Examples 1 to 3) either the metal source, e.g., litharge, or the organic acid was added to all other reactants at an elevated temperature as indicated, with total reflux used at times to control the reacting temperature. All batch products were clarified with diatomaceous earth and filtration; and dehydration and concentration were effected by vacuum distillation.

EXAMPLE 4

| | |
|---|---|
| 780 g PbO | Reacted well at 170F, clarified, concentrated to 1495 g at 48.0% Pb. |
| 378 g C9 Acid | M/A: 2.94 |
| 1000 g Cellosolve | %G: 106.3 |
| | Viscosity I |
| | Color 5 |
| | % NVM 84.9 |
| | Lbs./Gallon 14.82 |
| | LOM (+) |

The final product is a mobile liquid, the constitution of which in terms of litharge, the acid and Cellosolve as mole fractions is 0.34 of litharge, 0.23 of isononanoic acid and 0.43 of Cellosolve.

DRIER PERFORMANCE OF LEAD PRODUCT

As a control sample and product test sample, two samples of a commerical, linseed modified, long oil alkyd vehicle containing 60% solids were adjusted to the following drier metals content (NVM basis): 0.270% Pb, 0.034% Co, 0.038% Ca, 0.059% Mn; the latter three metals in both samples, and the lead in the control being provided by 12% cobalt, 8% calcium, 12% manganese and 36% lead commercial drier products manufactured from a standardized blend of synthetic, branched chain, saturated carboxylic acids. To the product test sample, the product of Example 4 was added in an amount to contribute the same lead content as maintained in the control.

After aging for 24 hours, the samples were applied to coated Morest charts in one mil wet film thickness, and the drying times were determined with Gardner Improved Drying Time Recorders, at 72F and 50% relative humidity. The observed through dry times were:

| | |
|---|---|
| Product Sample | 6¾ hours; |
| Control Sample | 6¾ hours. |

When the product of Example 4 was further tested for stability by diluting it with 20 parts of mineral spirits, the solution remained clear for over 96 hours; and in an oil solubility test by diluting it with ten volumes of raw linseed oil, the solution remained clear for more than 2 hours.

COMPARATIVE EXAMPLES (A–F)

A. By the procedure of U.S. Pat. No. 3,124,475, a mixture by weight of
- 279 parts, commercial mixture of isomeric trimethyl hexanoic acids, (AN 352),
- 423 parts of mineral spirits was heated to 210° F.; (this being equivalent to a mixture of
- 302 parts of isomeric trimethyl heptanoic acids, of acid number 326 and 400 parts of mineral spirits) and
- 261 parts of litharge was added.

After heating at 240°–250° F until substantially dry, followed by admixture of 10 parts of filter-aid, the mixture was filtered, and sufficient mineral spirits was added to the filtrate to reduce its lead content to 24%.

The product, a basic lead drier containing 1.34 equivalents of lead for each equivalent of acid, was a stable, clear liquid readily soluble in linseed oil.

B. With the same acid as in (A), another preparation was attempted, with M/A of 3 (actually 2,95/1), by heating to 210° F a mixture of
- 127 parts by weight of the acids and
- 527 parts of mineral spirits; then
- 261 parts litharge addition, and heating to 240°–250° F.

During and after the addition of the last 40% of the litharge there was no visible sign of reaction. The reaction mix became extremely viscous and opaque, and had the characteristic color of litharge. With gradual temperature increase to 330° F over a 6 hour period, there was no further change in appearance.

With cooling, the product solidified to a hard, opaque yellow mass, in which uncombined litharge was evident; and which could not be dissolved in mineral spirits or linseed oil. It was obviously a heterogenous mixture of no utility as drier, when thus prepared. With this putative lead soap, because of its hard, solid massive form, it was impossible to form a homogeneous composition by mechanical means when treated with 137 parts of Cellosolve.

C. By this invention, a mixture by weight of
- 127 parts trimethyl hexanoic acid with
- 575 parts Cellosolve (replacing mineral spirits of "B") was heated to 150° F;
- 261 parts of litharge was added.

After refluxing one-half hour at 249° F, and cooling to 130° F, sufficient Cellosolve was added to increase the batch to 1,000 parts by weight. After admixing ten parts of filter-aid and filtering, the filtrate was vacuum distilled to remove excess Cellosolve, yielding about 500 parts of a clear, mobile liquid containing 48% lead. This product, stable and readily soluble in linseed oil, remained so upon further dilution of 24% lead content with mineral spirits.

D. In a procedure similar to "C",
- 90 parts 2-ethylhexoic acid, (for the acid of "B"), and
- 353 parts of Cellosolve were heated to 150° F.
- 261 parts of litharge was added and the batch was heated to 250° F and mixed for 2 hours.

After addition of 10 parts of filter-aid and filtering, excess Cellosolve was vacuum distilled from the filtrate, producing about 500 parts of a clear, mobile, stable liquid, containing 48% lead and was readily soluble in linseed oil.

E. In another preparation, litharge was refluxed with Cellosolve for some hours; the unreacted litharge was filtered off; and the clear liquid product was concentrated by distilling under vacuum until it began to darken. The concentrated product was a mobile liquid containing 60% lead. When this liquid was evaporated at 105C in a "non-volatile" determination, a brown amorphous mass containing 76% lead was obtained.

Since litharge is a yellow powder containing 92.5% lead, it is therefore believed that the litharge was present in the product in a reacted i.e., combined, form of a lead alkoxyalkoxide type rather than a simple solution. The amorphous mass is apparently a decomposition product derived from the lead alkoxy alkoxide.

However, in this procedure "E" the metal conversion is poor, with the major part of the litharge unreacted, and concentration by distillation tends to darken the product. Moreover, the product itself when diluted with 20 volumes of mineral spirits shows some precipitation; and linseed oil solutions of this product tend to solidify upon even 48 hours storage. Hence product -and-process-wise, this preparation is inferior to the described preparation of the carboxylate-ethoxyethoxide type compositions of this invention, which are clear, relatively mobile, soluble in mineral spirits without precipitation of litharge or other solids and produce linseed oil solutions which are clear even after two hours where a 24% lead solution is mixed with five volumes of linseed oil.

Particularly to be noted is the fact that the five-carbon acid products of isopentanoic acid and of mixtures with other acids produced in accordance with the invention are soluble in mineral spirits.

Since even isopentanoic acid, so also 2-ethylhexoic acid, as well as trimethyl hexanoic acid can be employed with attainment of metal/acid ratios for either acid that are much higher than any attainable by the prior art procedures described, for example in the U.S. Pat. No. 3,124,475, it is therefore believed that here there is involved a novel type of composition as produced from the described process or method.

F. By a distinct procedure there were reacted the following:
- 1040 g PbO total, [0.33 total]
- 504 g isononanoic Acid [0.23]
- 536 g Cellosolve [0.44]

The acid was reacted with 371 g of the litharge at 240° F to produce a normal anhydrous soap.

The soap batch was cooled to 200° F and diluted with 100 g of Cellosolve. A slurry of 669 g of litharge in 436 g of Cellosolve was added to the normal anhydrous soap and refluxed for 2 hours. The batch was clarified to yield 2040 g of clear liquid containing 47.6% lead and 0.88% $H_2O$.

The M/A ratio of the reactants was 2.92. The product resulted from heating the reactants together under conditions which liberate water from the normal soap, but retain any additional water arising from the treatment of the normal soap with additional litharge and with Cellosolve. Unlike the products obtained by treatment under conditions where this water is not retained, the product is not soluble in linseed oil; though soluble in hydrocarbons and otherwise useful.

Further examples of compositions produced with various acids or acid mixtures, and various glycols or glycol ethers or mixtures thereof, absent mineral spirits, are given in Examples 5-1 to 5-18 for lead, Example 6 for barium; in the presence of mineral spirits in Examples 7-1 to 7-9 for lead; in Examples 8-1 to 8-5 for nickel; in Examples 9-1 and 9-2 for cobalt, followed by disclosure for manganese containing compositions according to the invention.

EXAMPLE 5-1

| | | |
|---|---|---|
| 520 g PbO | [0.37] | Reacted at 170F, clarified concentrated to 998 g at 48.0% Pb. |
| 252 g C9 Acid | [0.25] | M/A : 2.94 |
| 48 g triethylene glycol | | %G : 106.3 |
| 80 g Carbitol | [Mixture in excess of 0.38] | |
| 1240 Cellosolve | | |

| | | |
|---|---|---|
| 364 g PbO | [0.17] | Reacted well at 150F concentrated to 48.1% Pb. |
| 176 g C9 Acid | [0.12] | M/A : 2.94 |
| 600 g Cellosolve | [0.71] | %G : 106.3 |
| | | Viscosity J |
| | | Color 5 |
| | | % NVM 85.2 |
| | | Specific Gravity 1.780 |
| | | LOM (+) |

The final product is a liquid composition resulting from the reaction by heating together of 0.37 mol fraction litharge, 0.25 mol fraction of isononanoic acid and more than 0.38 mol fraction of mixed glycol ethers; the excess of the latter over 0.38 mol fraction along with water of reaction, being removed by vacuum distillation.

EXAMPLE 5-2

| | | |
|---|---|---|
| 364 g PbO | [0.17] | Reacted well at 150F concentrated to 48.1% Pb. |
| 176 g C9 Acid | [0.12] | M/A : 2.94 |
| 600 g Cellosolve | [0.71] | %G : 106.3 |
| | | Viscosity J |
| | | Color 5 |
| | | % NVM 85.2 |
| | | Specific Gravity 1.780 |
| | | LOM (+) |

The final product is a mobile liquid composition, the constitution of which in terms of the reactants, the litharge, the acid and Cellosolve, as mol fractions is 0.34 litharge, 0.23 isononanoic acid and 0.43 Cellosolve.

EXAMPLE 5-3

| | |
|---|---|
| 520 g PbO | Reacted well at 170F, clarified, concentrated to 996 g at 48.0% Pb. |
| 252 g C9 Acid | M/A : 2.94 |
| 80 g Carbitol | %G : 106.3 |
| 1000 g Cellosolve | |

The final product is a liquid composition, the constitution of which in terms of litharge, the acid and glycol ethers, as mol fractions is 0.35 litharge, 0.24 isononanoic acid and 0.41 mixed glycol ethers.

EXAMPLE 5-4

| | |
|---|---|
| 431 g PbO | Reacted at reflux 260F, clarified, concentrated to 937 g at 42.0% Pb. |
| 350 g naphthenic acid (AN 207) | M/A : 2.94 |
| 1432 g Cellosolve | %G : 106.3 |
| | % H$_2$O Trace |
| | Viscosity Z to Z-1 |
| | % NVM 90.8 |

The final product is a mobile liquid composition, the constitution of which in terms of litharge, the acid and Cellosolve as mol fractions is 0.26 litharge, 0.18 naphthenic acid, and 0.56 Cellosolve.

EXAMPLE 5-5

| | |
|---|---|
| 473 g PbO | Reacted at reflux 260F, clarified, concentrated to 954 g at 45.6% Pb. |
| 317 g naphthenic acid (AN 207) | M/A : 3.58 |
| 20 g water | %G : 63.7 |
| 1074 g Cellosolve | |

The final product is a liquid, the constitution of which in terms of litharge, the acid and Cellosolve as mol fractions is 0.38 of litharge, 0.21 naphthenic acid and 0.41 Cellosolve.

| | |
|---|---|
| 520 g PbO | Reacted well at reflux, 260F clarified, concentrated to 1002 g at 48.0% Pb. |
| 228 g C8 Acid | M/A : 3.25 |
| 1000 g Cellosolve | %G : 128.0 |
| | Viscosity A |

The final product is a very thin liquid, the constitution of which in terms of litharge, the acid and Cellosolve as mol fractions is 0.34 litharge, 0.21 2-ethylhexoic acid and 0.45 Cellosolve.

EXAMPLE 5-7

| | |
|---|---|
| 520 g PbO | Reacted well at 160F, clarified, concentrated to 986 g at 48.0% Pb. |
| 224 g C9 Acid | M/A : 3.25 |
| 500 g Cellosolve | %G : 128.0 |
| | Viscosity D |

The final product is a very thin liquid, the constitution of which in terms of litharge, the acid and Cellosolve as mol fractions is 0.33 litharge, 0.21 isononanoic acid, and 0.46 Cellosolve.

EXAMPLE 5-8

| | |
|---|---|
| 520.0 g PbO | Reacted at 250F, clarified, concentrated to 986 g at 48.0% Pb. |
| 179.5 g C8 Acid | M/A : 3.98 |
| 1400.0 g Cellosolve | %G : 180.6 |
| | Viscosity A-1 |
| | LOM (+) |

The final product is a very thin liquid, the constitution of which in terms of litharge, the acid and Cellosolve as mol fractions is 0.34 litharge, 0.17 2-ethylhexoic acid and 0.50 Cellosolve.

EXAMPLE 5-9

| | |
|---|---|
| 520 g PbO | Reacted at reflux 250F, clarified, concentrated to 923 g at 48.0% Pb. |
| 180 g C8 Acid | M/A : 3.80 |
| 1400 g Methyl Cellosolve | %G : 166.5 |
| | Viscosity A-4 |
| | LOM (+) |

The final product is a very thin liquid, the constituion of which in terms of litharge, the acid and glycol ether, as mol fractions is 0.31 litharge, 0.16 2-ethylhexoic acid and 0.53 methyl Cellosolve.

EXAMPLE 5-10

| | |
|---|---|
| 520 g PbO | Reacted at reflux 260F, clarified, concentrated to 982 g at 48.0% Pb. |
| 234 g ND Acid | M/A : 2.61 |
| 700 g Cellosolve | %G : 119.1 |
| | Viscosity I |

The final product is a thin liquid, the constitution of which in terms of litharge, the acid and Cellosolve, as mol fractions, is 0.28 litharge, 0.22 neodecanoic acid and 0.50 Cellosolve.

EXAMPLE 5-11

| | |
|---|---|
| 520.0 g PbO | Reacted at reflux 250F, clarified, concentrated to 979 g at 48.0% Pb. |
| 108.0 g C9 Acid | M/A : 3.25 |
| 54.5 g C8 Acid | %G : 130.4 |
| 54.5 g Neo Acid Blend (AN 363) | Viscosity A |
| 700.0 g Methyl Cellosolve | LOM (+) |

The final product is a very thin liquid, the constitution of which in terms of litharge, the acid and glycol ether, as mol fractions, is 0.31 litharge, 0.19 mixed 2-ethylhexoic, isononanoic acids and neononanoic acids, and 0.50 methyl Cellosolve.

EXAMPLE 5-12

| | |
|---|---|
| 520 g PbO | Reacted at reflux 260F, clarified, concentrated to 971 g at 46.8% Pb. |
| 314 g naphthenic acid (AN 207) | M/A : 3.80 |
| 1575 g Cellosolve | %G : 64.3 |
| | Viscosity N |
| | LOM (+) |

The final product is a mobile liquid, the constitution of which in terms of litharge, the acid and cellosolve, as mol fractions is 0.39 litharge 0.21 naphthenic acid and 0.40 Cellosolve.

EXAMPLE 5-13

| | | |
|---|---|---|
| 1170 g PbO | [0.45] | Reacted at 290F, i.e., about 143C; clarified Pb : 35.9% |
| 950 g absorption oil | | M/A : 3.11 |
| 207 g Carbitol | [0.26] | %G : 74.7 |
| 207 g dipropylene glycol | | Viscosity D |
| 555 g C9 Acid | [0.29] | Color 1 |
| | | % H₂O : 0.33 |

The final product is a mineral oil solution of the composition resulting from the reaction. The mineral oil solvent contains 30% by weight of mixed glycol and glycol ether, with respect to the weight of their mixture with the solvent, or SR is 30%. This product is useful not as a paint drier, but as a fuel and lubricant additive.

EXAMPLE 5-14

| | |
|---|---|
| 520 g PbO | Reacted at reflux, 250F, clarified, concentrated to 956 g at 48.0% Pb. |
| 171 g Neo Acid Blend (AN 363) | M/A : 4.03 |
| 50 g Butyl Cellosolve | %G : 161.5 |
| 1300 g Methyl Cellosolve | Viscosity A-1 to A-2 |
| | Color 1 |
| | LOM (+) |

The final product is a very thin liquid, the constitution of which the terms of litharge, the acid and glycol ethers as mol fractions is 0.33 litharge, 0.16 neononanoic acids, and 0.51 mixed glycol ethers.

EXAMPLE 5-15

| | |
|---|---|
| 390 g PbO | Reacted at 240F, clarified, concentrated to 980 g at 36.0% Pb. |
| 333 g naphthenic Acid (AN 178) | M/A : 3.24 |
| 1090 g Cellosolve | %G : 86.1 |
| | Viscosity A |
| | Color 5— |
| | % NVM 74.0 |
| | Lbs./Gallon 12.15 |
| | LOM (+) |

The final product is a very thin liquid, the constitution of which in terms of litharge, the acid and Cellosolve, as mol fractions, is 0.29 litharge, 0.18 naphthenic acid and 0.53 Cellosolve.

EXAMPLE 5-16

| | |
|---|---|
| 520 g PbO | Reacted under reflux, clarified concentrated to 911 g at 49.9% Pb. |
| 830 g Cellosolve | Diluted to 48% Pb with Cellosolve |
| 140 g isopentanoic Acid | M/A : 3.35 |
| | Viscosity A-3 |
| | LOM (+) |

The final product is a very thin liquid, the constitution of which in terms of litharge, the acid and Cellosolve, as mol fractions, is 0.30 litharge, 0.18 isopentanoic acid and 0.52 Cellosolve.

EXAMPLE 5-17

| | |
|---|---|
| 520 g PbO | Reacted under reflux, clarified, concentrated to 924 g at 50.7% Pb |
| 830 g Cellosolve | Diluted to 48% Pb |
| 97 g C8 Acid | M/A : 3.34 |
| 73 g isopentanoic Acid | LOM (+) |

The final product is a liquid, the constitution of which in terms of litharge, the acid and Cellosolve, as mol fractions, is 0.30 litharge, 0.19 mixed 2-ethylhexoic and isopentanoic acids, and 0.51 Cellosolve.

EXAMPLE 5-18

| | |
|---|---|
| 520 g PbO | Reacted under reflux, clarified, concentrated to 910 g |

830 g Cellosolve
110 g isopentanoic acid
35 g Mixed Neo Acids
(AN 363)

at 50.5% Pb.
Diluted to 48% Pb
M/A : 3.5
LOM (+)

Color : 4 Gardner
15.0 Lbs. per Gallon

The final product is a liquid, the constitution of which in terms of litharge, the acid and Cellosolve, as mol fractions is 0.30 litharge, 0.17 mixed neo acids and isopentanoic acid, and 0.53 Cellosolve.

EXAMPLE 6

A barium product was similarly produced by the procedure of Examples 1 and 2 with a reaction mix comprising:
282 g barium hydroxide monohydrate,
156 g C9 Acid (isononanoic acid), in 1140 g Cellosolve.

The barium source reacted completely, though in this mixture the metal/acid ratio was 3/1.

EXAMPLE 7-1

| | | |
|---|---|---|
| 522 g PbO | [0.43] | Reacted well at 150F, clarified, concentrated to 47.8% Pb. |
| 297 g C9 Acid | [0.35] | M/A : 2.50 |
| 28 g IPA | | %G : 61.3 |
| 182 g polypropylene glycol | [0.22] | Viscosity >Z-6 |
| 1000 g MS | | |

The isopropyl alcohol here and the other examples facilitates the removal of water from the batch in an azeotrope distillate. The final product (about 968 g) is a mineral spirits solution of the composition resulting from the reaction. The ratio of the weight of glycol represented in the product, to the sum of that weight plus the weight of remaining mineral spirits solvent is 79%; this and analogous ratios here and in certain others of examples for convenience being expressed as a percentage and arbitrarily called the "solvent ratio", SR.

EXAMPLE 7-2

| | | |
|---|---|---|
| 522 g PbO | [0.42] | Reacted well at 150F, clarified, concentrated to 48.0% Pb. |
| 297 g C9 Acid | [0.34] | M/A : 2.50 |
| 28 g IPA | | %G : 61.3 |
| 182 g Carbitol | [0.24] | Viscosity >Z-6 |
| 1000 g MS | | SR : 80% |

The final product (about 965 g) is a mineral spirits solution of the composition resulting from the reaction.

EXAMPLE 7-3

| | | |
|---|---|---|
| 522 g PbO | [0.45] | Reacted at 150F, clarified, concentrated to 47.6% Pb. |
| 297 g C9 Acid | [0.37] | M/A : 2.5 |
| 28 g IPA | | %G : 61.3 |
| 182 g tripropylene glycol | [0.18] | Viscosity >Z-6 |
| 1000 g MS | | SR : 77% |

The final product (about 972 g) is a mineral spirits solution of the composition resulting from the reaction.

EXAMPLE 7-4

| | | |
|---|---|---|
| 522 g PbO | [0.43] | Reacted well at 150F, clarified, concentrated to 47.0% Pb. |
| 297 g C9 Acid | [0.35] | M/A : 2.50 |
| 28 g IPA | | %G : 61.3 |
| 182 g triethylene glycol | [0.22] | Viscosity >Z-6 |
| 1000 g MS | | SR : 80% |

The final product (about 1030 g) is a mineral spirits solution of the composition resulting from the reaction.

EXAMPLE 7-5

| | | |
|---|---|---|
| 522 g PbO | [0.45] | Reacted at 150F, clarified, concentrated to 45.4% Pb. |
| 297 g C9 Acid | [0.37] | M/A: 2.50 |
| 28 g IPA | | %G : 61.3 |
| 182 g tetraethylene glycol | [0.18] | Viscosity >Z-6 |
| 1000 g MS | | SR : 63.5% |

The final product (about 1020 g) is a mineral spirits solution of the composition resulting from the reaction.

EXAMPLE 7-6

| | | |
|---|---|---|
| 537 g PbO | [0.43] | Reacted well at 150F, clarified, concentrated to 1000 g at 48.1% Pb. |
| 297 g C9 Acid | [0.34] | M/A : 2.58 |
| 28 g IPA | | %G : 61.3 |
| 61 g triethylene glycol | [0.23] | Viscosity >Z-6 |
| 121 g Carbitol | | SR : 79% |
| 1000 g MS | | |

The final product is a mineral spirits solution of the composition resulting from the reaction.

EXAMPLE 7-7

| | | |
|---|---|---|
| 522 g PbO | [0.42] | Reacted well at 150F, clarified, concentrated to 42.0% Pb. |
| 218 g C9 Acid | [0.28] | M/A : 2.98 |
| 28 g IPA | | %G : 91.7 |
| 80 g dipropylene glycol | [0.30] | Viscosity Z |
| 20 g triethylene glycol | | SR : 43% |
| 100 g Carbitol | | |
| 1000 g MS | | |

The final product is a mineral spirits solution of the composition resulting from the reaction.

EXAMPLE 7-8

| | | |
|---|---|---|
| 455 g PbO | [0.47] | Reacted well at 150F, clarified, concentrated to 872 g at 48.0% Pb. |
| 220 g C9 Acid | [0.33] | M/A : 2.90 |
| 28 g IPA | | %G : 50.9 |
| 42 g dipropylene glycol | [0.20] | SR : 47% |
| 70 g Carbitol | | |
| 3 g acetic Acid | | |
| 1000 g MS | | |

The acetic acid promotes the reaction. The final product is a mineral spirits solution of the composition resulting from the reaction.

EXAMPLE 7-9

| | | |
|---|---|---|
| 520 g PbO | [0.41] | Reacted well as 150F, clari- |

-continued

| | | |
|---|---|---|
| | | fied, concentrated to about 48% lead |
| 296 g C9 Acid | [0.31] | M/A : 2.54 |
| 224 g dipropylene glycol | [0.28] | %G : 75.7 |
| 1000 g MS | | Viscosity >Z-6 |

The final product is a viscous liquid resulting from the reaction. All mineral spirits was removed from the product by distillation.

EXAMPLE 7-10

| | | |
|---|---|---|
| 255 g PbO | [0.36] | Reacted at 240F, clarified, 1000 g at 24.0% Pb. |
| 120 g dipropylene glycol | [0.28] | M/A : 2.0 |
| 341 g L-5 Tall Oil Fatty Acid | [0.36] | %G : 35.2 |
| 299 g MS | | SR : about 29% |

The final product is a mineral spirits solution of the composition resulting from the reaction. Again, as in the other examples with a product composition in a hydrocarbon solution, the "solvent ratio" amounts to more than 25%, specifically here, about 29%.

Likewise compositions soluble in hydrocarbons and useful as driers and representing a metal/acid ratio much higher than usual, generally with appreciable negative acid number, were obtained with nickel, cobalt and manganese.

Such compositions were derived from powdered manganese with naphthenic acid, methyl Cellosolve and polypropylene glycol (PPG), from powdered nickel, with Cellosolve and polypropylene glycol and an acid, namely neodecanoic acid, commercial (C : 9–13) neo acids, 2-ethylhexoic acid and mixtures of these; from cobalt powder with Cellosolve (with and without PPG) or alternatively dipropylene glycol, diethylene glycol, methyl Cellosolve, and various acids, namely naphthenic acid, 2-ethylhexoic acid, (C : 9–13) neo acids, (acid numbers of 340 to 365) and mixtures of such acids, in this case the batches including a hydrocarbon medium, generally mineral spirits but also others such as Xylene being used.

EXAMPLE 8-1

There was heated for 12 hours at about 172°–180°F a batch comprising:

| | |
|---|---|
| 200 g. | nickel powder (3.41 moles) |
| 300 g. | C8 Acid (2.03 moles, 380 acid number) |
| 455 g. | MS solvent |
| 6.5 g. | sulfuric acid |
| 1.1 g. | potassium iodide |
| 62 g. | water |
| 30 g. | polypropylene glycol (0.2 moles) |
| 250 g. | 2-ethoxyethanol (2.79 moles) |

The contained aqueous solution of potassium iodide and sulfuric acid promotes the initial reaction; but the water had to be removed (preferably done under vacuum, at about 240°F) to complete the formation of the complex. The mineral spirits was removed by distillation.

The relative amounts of 2-ethylhexoic acid (2.03 moles) and alkoxyalkanols (total 2.99 moles) used in the above batch were, mol percent: 40.4% acid, 4% polypropylene glycol, and 55.6% 2-ethoxyethanol.

Analysis of the liquid product obtained showed the following:

| | | | |
|---|---|---|---|
| % Ni | 15.6 | M/A | 1.62 |
| Base Number | 114 | M/Alk | 3.0 |
| % NVM | 79 | Spec. Grav. | 1.095 |
| | | Viscosity | K |

EXAMPLE 8-2

There was heated for four hours at about 172°–180°F a batch comprising:
400 g nickel powder, (6.81 moles, excess)
800 g C9-13 Acid, (AN 360, ave. mol. weight 156, 5.13 moles)
1100 g MS
2.5 g potassium iodide dissolved in 150 g water, (reaction catalyst)
16 g sulfuric acid (reaction catalyst)
50 g polypropylene glycol (mol. weight 150, 0.33 moles)
150 g Cellosolve (mol. weight 90, 1.67 moles).

The relative amounts in mol percentages, of glycol or glycol ethers (total 2.0 moles) to acid were: 72.0% mixed neo acids, 4.6% polypropylene glycol, and 24.4% Cellosolve.

After filtering off unreacted excess nickel, the end product was a mineral spirits solution containing 10% nickel and having a base number of 26.7. It is noted that commercial nickel carboxylate solution, generally contain 10% nickel, but usually have acid numbers of about 65.

EXAMPLE 8-3

Similarly was heated for about 10½ hours (initially between 160°–180°F and terminally for 3 hours between 200°–282°F), a batch comprising:
400 g nickel powder (6.81 moles)
420 g C 9-13 mixed neo acids, (AN 334) (average mol weight 168, 2.5 moles)
370 g C8 Acid, (AN 379, ave. mol. weight 148, 2.5 moles)
1000 g MS
2.5 g potassium iodide dissolved in 150g H₂O
16 g sulfuric acid
75 g polypropylene glycol (0.5 moles)
300 g Cellosolve (3.3 moles).

The relative acid, glycol and glycol-ether amounts in mol. percentages were: 56.7% mixed carboxylic acids, 5.7% glycol, and 37.6% glycol ether. The water of the potassium iodide solution was sufficient to form a distinct phase in the reaction batch.

After filtration, much of the mineral spirits was distilled off under vacuum of about 30mm Hg. A liquid containing 15% Ni and 88% NVM was obtained, with a base number of 63.

EXAMPLE 8-4

For about 7 hours, there was heated at about 170°–184°F a batch comprising:
500 g nickel powder (8.5 moles)
825 g C 9-13 carbon mixed neo acids, (AN 334) (ave. mol. weight 168, 5 moles)
600 g MS
16 g sulfuric acid
2.5 g potassium iodide in 150 g water
75 g polypropylene glycol (0.5 moles)
600 g Cellosolve (6.7 moles).

The relative amounts of acid to glycol and glycol ether in mol percentages were: 41.0% neo acids, 4.0% glycol, and 55.0% glycol ether.

The batch was filtered while hot and the mineral spirits distilled off under vacuum to give in distinct samples about 10% and 12% nickel respectively.

The 10% product had the following properties:

| | |
|---|---|
| Base number | 34.5 |
| % NVM | 60.7 |
| Specific Gravity | 0.984 |
| Viscosity | A-5 |

By reducing the quantity of mineral spirits in the composition to raise the nickel content to 12%, the viscosity was increased to Gardner D. With apparently complete stripping of mineral spirits and cooling, a solid product, 16.3% nickel, resulted. The mol percentage of components indicate that the composition does not contain a proponderance of carboxylate.

EXAMPLE 8-5

By similar procedures a batch was prepared with neodecanoic acid (176 ave. mol. weight, AN 319) by weight percent as follows:

| | | |
|---|---|---|
| nickel powder | 10.0 | |
| neodecanoic acid | 48.0 | [0.41] |
| potassium iodide in $H_2O$ | 0.1 | ($H_2O$ phase 5% of total) |
| sulfuric acid | 0.9 | |
| mineral spirits | 5.2 | |
| polypropylene glycol | 4.1 | [0.04] |
| Cellosolve | 32.7 | [0.55] |

A portion of the product concentrated to 10% nickel had a base number of 45.8.

EXAMPLE 9-1

By similar procedures there was reacted a batch comprising:
- 350 g cobalt powder (excess)
- 640 g naphthenic acid (AN 170, ave. mol. weight 330)
- 70 g polypropylene glycol (mol. weight 150)
- 300 g Cellosolve (mol weight 90)
- 15 g acetic acid (promotor)
- 150 g water (promotor).

The product was a liquid containing 7.58% cobalt and having a base number (negative acid number) of 92.3 or computed to a 6% concentration, a base number 73; whereas commercial cobalt naphthenate has an acid number of zero or slightly positive.

EXAMPLE 9-2

With a batch composition by weight % comprising:

| | |
|---|---|
| cobalt | 6.0 |
| naphthenic acid (AN 172) | 26.8 |
| mineral spirits | 56.3 |
| acetic acid (catalyst) | 0.7 |
| Cellosolve | 10.9 |
| water to form a distinct phase, | | there was obtained by like procedures a liquid product which when adjusted to 6% cobalt had a base number 64.

The water is required in sufficient amount, here and in other direct metal reactions, e.g., nickel, cobalt, manganese, to form a distinct phase, usually about 5% being sufficient, but depending of course on miscibility in other components.

With an increase in the Cellosolve-to-acid ratio, higher cobalt contents have been obtained in liquid products, with higher base numbers, e.g., 9% cobalt with a base number of 100, and 12% with a base number of 118.

Manganese compositions, similarly made using excess powdered manganese in the batch, but also isoamyl phosphoric acid to the extent of about 1.7 to ¼ of naphthenic acid equivalents, resulted in liquid products of low viscosity, manganese contents of about 9.5% to 10.4% and acid number of −54 to −122.

What is claimed is:

1. A hydrocarbon-soluble composition comprising the reaction product of
    a polyvalent metal in a form
        selected from the group consisting of free metals, oxides, hydroxides, acetates, and carbonates or the polyvalent elements cobalt, nickel and manganese, and mixtures thereof,
    with a mixture of reactants comprising
        at least one acid substance selected from the group consisting of higher fatty acids containing at least five carbon atoms, alkoxy and phenoxy fatty acids, ether and thioether monocarboxylic acids, tall oil fatty acids and naphthenic acids, and
        at least one other substance, selected from the group consisting of members within the formula $$[R_n(OR')_zOH]_z$$

wherein
    R is a hydrogen or an alkyl radical containing 1 to 10 carbon atoms;
    $n$ is 0 or 1;
    R' is an alkylene radical which contains from 2 to 4 carbon atoms and may have substituent hydroxyl groups;
    y has a value of from 0 to 4;
    z has a value of 2 when $n$ is zero, and a value of 1 when $n$ is 1 and R is hydrogen or alkyl;
    the above described reactants being induced to reaction by heating;
    the ratio of the number of equivalents of the metal moiety to the acid moiety being not less than 1.0 and the equivalents ratio of the metal moiety to the said other substance being at least 0.5;
    said composition having a negative acid number.

2. A composition as described in claim 1, wherein said acid substance is selected from the group consisting of an acylic monocarboxylic acid having from 5 to 13 carbons, naphthenic acid, tall oil acids, and mixtures thereof.

3. A composition as described in claim 1 in which a plurality of substances is used each within the said formula.

4. A composition as described in claim 1, wherein said other substance is selected from the group consisting of 2-ethoxyethanol, 2-methoxyethanol, 2-butoxyethanol, diethylene glycol monoethyl ether, diethylene glycol, triethylene glycol, tetraethylene glycol, dipropylene glycol, tripropylene glycol, polypropylene glycol, ethylene glycol, and sorbitol.

5. A hydrocarbon-soluble composition suitable as a drier additive in drying type coating formulations, comprising the reaction product of
    a polyvalent metal in a form selected from the group consisting of free metals, oxides, hydroxides, acetates, and carbonates or the polyvalent elements lead, cobalt, nickel and manganese, and mixtures thereof, with a mixture of reactants comprising
at least one acid substance selected from the group consisting of higher fatty acids containing at least five carbon atoms, alkoxy and phenoxy fatty acids, ether and thioether monocarboxylic acids, tall oil fatty acids, and naphthenic acids, and
at least one other substance, selected from the group consisting of members within the formula

wherein
R is a hydrogen or an alkyl radical containing 1 to 10 carbon atoms;
$n$ is 0 or 1;
R' is an alkylene radical which contains from 2 to 4 carbon atoms and may have substituent hydroxyl groups;
$y$ has a value of from 0 to 4;
$z$ has a value of 2 when $n$ is zero, and a value of 1 when $n$ is 1 and R is hydrogen or alkyl;
the above described reactants being induced to reaction by heating;
the ratio of the number of equivalents of the metal moiety to the acid moiety being not less than 1.0 and, when the metal is lead, being not less than 1.5;
the equivalents ratio of the metal moiety to the said other substance being at least 0.5;
said composition having a negative acid number, and a metal content by weight percent in the case of lead exceeding 36% and in the case of the other said metals of at least 10%.

6. A composition as described in claim 1, in solution in a hydrocarbon.

7. A composition as described in claim 1, in solution in mineral spirits.

8. A composition as described in claim 1 in solution in an excess of said second substances.

9. A composition as described in claim 1, wherein the metal is cobalt.

10. A composition as described in claim 1, wherein the metal is nickel.

11. A composition as described in claim 1, wherein the metal is manganese.

12. A method for preparing a composition of the type described in claim 1, which comprises:
heating a quantity of a polyvalent metal powder, oxide or hydroxide selected from the first said group with a carboxylic acid selected from the second said group and a member of the third said group;
the metal to acid equivalents ratio being at least 1.0, and the equivalents ratio of metal to the selected member or members of said third group being at least 0.5,
the reaction being carried out in a temperature range between approximately 65°C and 143°C;
the heating being carried on until the reaction mixture batch is substantially anhydrous;
the reaction being carried out in substantial absence of any hydrocarbon with a boiling point as high as or higher than the selected member or members of said third group;
filtering the product composition;
and distilling off excess of any unreacted amount of the member of the said third group.

13. A method as described in claim 12, wherein a hydrocarbon solvent is used as a reaction medium diluent; the hydrocarbon being more volatile than the said other substances.

14. A method as described in claim 12, for preparing a composition, wherein:
the acid substance is selected from the group consisting of a fatty acid having from 5 to 13 carbon atoms, naphthenic acid, tall oil acid and mixtures thereof.

15. A method as described in claim 14, wherein said other substance is selected from the group consisting of 2-ethoxyethanol, 2-methoxyethanol, 2-butoxyethanol, diethylene glycol monoethyl ether, diethylene glycol, triethylene glycol, tetraethylene glycol, dipropylene glycol, tripropylene glycol, polypropylene glycol, ethylene glycol, sorbitol and mixtures thereof.

16. A composition as described in claim 5, wherein said polyvalent metal is lead in the form of litharge; and the first said ratio is about 2 : 1.

17. A composition as described in claim 5, wherein said other substance is selected from the group consisting of 2-ethoxyethanol, 2-methoxyethanol, 2-butoxyethanol, diethylene glycol monoethyl ether, diethylene glycol, triethylene glycol, tetraethylene glycol, dipropylene glycol, tripropylene glycol, polypropylene glycol, ethylene glycol and sorbitol.

18. A composition as described in claim 17, wherein said acid substance is selected from the group consisting of an acylic monocarboxylic acid having from 5 to 13 carbons, naphthenic acid, tall oil acids, and mixtures thereof.

* * * * *

UNITED STATES PATENT OFFICE
CERTIFICATE OF CORRECTION

PATENT NO. : 3,941,606
DATED : March 2, 1976
INVENTOR(S) : Albert V. Collins and Richard E. Pearl It is certified that error appears in the above-identified patent and that said Letters Patent are hereby corrected as shown below:

Col. 1, line 65, for "form/normal" read --form normal--.

Col. 2, line 9, for "Synthesis" read --synthesis--;
line 16, for "composition structure" read --composition, structure--.

Col. 4, line 51, for "ored, appearance and the litharge has substantially" read -- ored appearance and the litharge had substantially--.

Col. 7, line 26, for "2,95/1" read --2.95/1--.

Col. 9, under the heading "Example 5-1", omit the material "364 g PbO ... LOM(+)".

Col. 10, at the space for an apparent line 30, (after "0.41 Cellosolve."), there should appear the heading --EXAMPLE 5-6 --.

Col. 18, line 19, for "carbonates or" read --carbonates of--.

Signed and Sealed this

Seventeenth Day of August 1976

[SEAL]

Attest:

RUTH C. MASON
Attesting Officer

C. MARSHALL DANN
Commissioner of Patents and Trademarks